Aug. 21, 1956 A. BARKIN Re. 24,196

THERMALLY CONTROLLED VAPORIZER

Original Filed Jan. 5, 1953

INVENTOR.
AARON BARKIN,
BY H. Lee Helms
ATTORNEY.

United States Patent Office

Re. 24,196
Reissued Aug. 21, 1956

24,196

THERMALLY CONTROLLED VAPORIZER

Aaron Barkin, New York, N. Y., assignor to Practical Electrical Products, Inc., Bronx, N. Y., a corporation of New York Original No. 2,713,628, dated July 19, 1955, Serial No. 329,707, January 5, 1953. Application for reissue March 9, 1956, Serial No. 570,659

7 Claims. (Cl. 219—40)

Matter enclosed in heavy brackets [ ] appears in the original patent but forms no part of this reissue specification; matter printed in italics indicates the additions made by reissue.

This invention relates to vaporizers adapted to vaporize substances as in conjunction with a steam jet, the vapors of which are beneficial to the respiratory system.

It is an object of this invention to provide a vaporizer adapted to continuously and gradually convert a supply of water safely into steam.

It is also an object of this invention to heat a volume of liquid to vaporization while in communication with a reservoir of said liquid without a substantial heating of the liquid in said reservoir.

It is a further object of this invention to provide a vapor confining dome adapted to hold a container of medicated liquid, said dome being provided with a jet orifice disposed adjacent the top of said container.

It is another object of this invention to provide a vaporizer dome having a container well wherein the base of said well is in communication with heated vapor disposed in said dome.

It is still another object of this invention to provide a vaporizer with a well disposed in and having an orifice communicating with a reservoir of liquid, said well being adapted to permit entrance of cool water therein but to prevent substantial exit of heated water therefrom.

Figure 1:
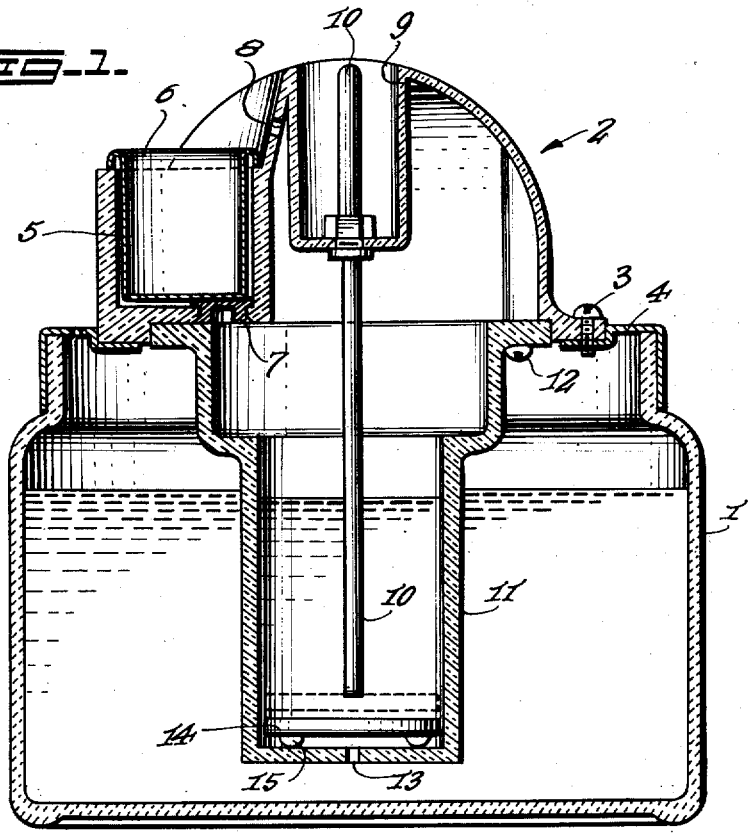
Figure 3:
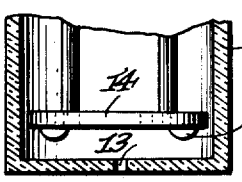
Figure 4:
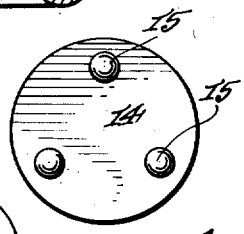
Figure 2:
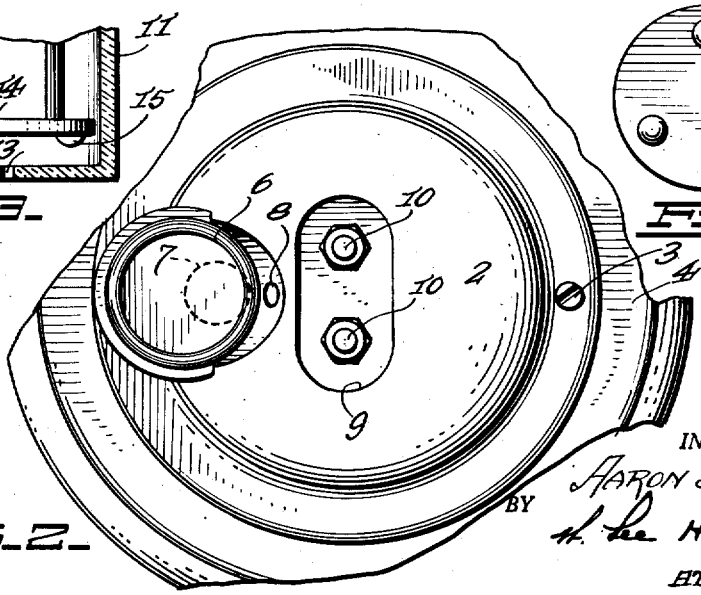

These and other objects of this invention will become apparent upon reading the following disclosure taken in conjunction with the drawing in which, Fig. 1 is a vertical section taken through the vaporizer showing a floating valve and indicating by dotted lines the movement of said valve, Fig. 2 is a top view, broken away in part, Fig. 3 is a detailed view showing the floating valve in its highest position, and Fig. 4 is a bottom view of an electrically nonconductive floating valve and showing its supporting legs.

Referring to the drawing a vessel or jar 1, for example, a glass jar is provided with a dome 2, preferably molded of plastic, secured by screw 3 to a circumferential enclosure 4, disposed between the base of dome 3 and the top of jar 1 in a vapor-tight relationship.

The dome 2 is provided with a vertical container well 5 having a container 6 therein, the base of said well 5 being in heat communication with the vapor within the dome 2, through a metal plug 7 adapted to contact container 6. A jet orifice 8 is disposed in the dome 2 adjacent the top rim of container 6. In operation, the medicated liquid disposed in container 6 is heated by metal plug 7, and the heated medicated vapors arising from the container are then dispersed by means of the steam jet issuing from jet orifice 8. The metal plug or insert 7 is preferably molded into the dome 2 during the molding operation.

A vertical electrode well 9 is also molded in said dome 2, the base of which is provided with a pair of apertures adapted to hold a pair of electrodes 10. The electrodes 10 which may be of graphite or metal, are secured to the base of well 9 by conventional means.

A vertical cylindrical vaporization well 11, preferably of plastic, is secured to the base of dome 2 by means of screw 12, said well 11 being disposed directly beneath said well 9. The base of well 11 is provided with a centrally disposed orifice 13 to effect passage of liquid from jar 1 to the interior of well 11.

A circular floating valve 14, preferably made of ceramic material, and having a diameter slightly less than the diameter of the cylindrical cavity of well 11 is provided with a plurality of supporting legs 15 adapted to maintain a space between the bottom of valve 14 and the top opening of orifice 13.

The bottoms of the spaced-apart parallel electrodes 10 are disposed a short distance above the bottom of well 11, thereby permitting the floating valve 14 disposed therebetween to be slightly raised for easy entrance of water from the reservoir jar 1 into well 11.

*It will be understood from the foregoing, that the floating valve 14 is a displaceable disc and that means are provided so that the disc cannot close the orifice 13 in the base of the well. Thus, even though the disc is termed a valve, liquid may enter the well through the orifice in the base of well at all times during operation of the vaporizer and liquid entering the well through the orifice will be diverted around the edges of the disc which is slightly smaller in diameter than the diameter of the cavity in the well before such liquid contacts the electrodes. It will also be seen that since the floating valve or displaceable disc 14 is made of ceramic material, it floats only in the sense that the disc may move upwardly relative to the base of the well under the influence of liquid flowing into the well through the orifice 13 in the base of the well.*

In operating the apparatus of this invention a small amount of an alkaline electrolyte, for example, borax is dissolved in the water disposed in the reservoir of jar 1. Upon placing the well 11 into the aqueous borax solution of jar 1, some of the solution passes through orifice 13 into the cavity of well 11 until the liquid surface inside well 11 is on a horizontal plane with the surface of the solution in jar 1. The borax solution on entering well 11 does so with force sufficient to raise floating valve 14, so filling up of well 11 is done in a minimum of time, despite the fact that orifice 13 is covered by valve 14 and that the clearance between the valve rim and the inside wall of well 11 is small.

Upon plugging the electrodes into an electrical circuit the passage of current between the electrodes and through the electrolyte solution, creates sufficient heat to cause steam formation in well 11 in about one minute. The steam thus formed is confined beneath dome 2 and heats metal plug 7 by contact therewith, and issues as a jet through orifice 8, which orifice 8 is of larger area than orifice 13. The formation of steam creates a slight pressure on the surface of the solution of well 11 but this solution is not substantially forced out of orifice 13, because of the resistance to its passage caused by the slight clearance between the rim of valve 14 and the interior wall of well 11, as well as because of the resistance to flow set up by the tortuous path which the solution must follow in passing from a point above valve 14 to the orifice 13.

Modifications of this invention include replacing orifice 8 with a plurality of orifices, and replacing plug 7 with a plurality of plugs, and also include replacing orifice 13 with a plurality of orifices. Furthermore, supporting legs 15, while shown as hemispherical studs, clearly may have other shapes and still be within the concept of this invention.

While this invention was described and shown by an illustrative embodiment, clearly its scope is broader than this embodiment and is that of the claims appearing herein.

Having described my invention, what I claim and desire to secure by Letters Patents is as follows:

1. A thermally controlled vaporizer for dispersing medicated vapors comprising an upright open mouth vessel for holding an aqueous electrolyte, a molded dome of dielectric material disposed over said vessel in vapor-tight relationship and having a container well therein, a cylindrical vertically disposed vaporization well of dielectric material secured to said dome in vapor-tight relation and disposed in said electrolyte and having an orifice in its base for passage of electrolyte from said vessel into said well, electrical heating rods secured to said dome and protruding into said electrolyte in said well for changing water into steam, and a metal plug communicating between said interior of the container well and the interior of said dome, whereby heat from the dome-confined steam heats said plug thereby heating vaporizable medicant disposed in said container well.

2. A thermally controlled vaporizer for dispersing medicated vapors comprising an upright vessel for holding an aqueous electrolyte, a plastic dome disposed over said vessel in vapor-tight manner and having a vertically disposed medicant container well therein, a cylindrical vertically disposed vaporization plastic well secured to said dome in vapor-tight relation and disposed in said electrolyte and having an orifice in its base for passage of electrolyte from said vessel into said well, heating rods secured to said dome and immersed in said electrolyte in said well for changing water into steam, and a disc valve having a plurality of legs floatably disposed in the bottom of said vaporization well intermediate the bottom of said electrodes and the orifice disposed in the base of said well, whereby the ease of introducing electrolyte solution above the valve in said well is greater than that of forcing out said solution by steam formed in said vaporization well.

3. A thermally controlled electrically heated vaporizer for vaporizing medicated liquid comprising an upright vessel for holding an aqueous electrolyte, a dome of insulating dielectric material disposed over said vessel and having an upright container well integrally molded therein, a cylindrical vertically disposed vaporization well of plastic material secured to said dome in vapor-tight relation and disposed in said electrolyte and having an orifice in its base for passage of electrolyte from said vessel into the vaporization well, electrically heating rods secured to said dome and disposed vertically in said electrolyte in said vaporization well for changing water into steam, a metal plug communicating between the interior of the container well and the interior of said dome, a metal container disposed in said container well and upon said plug, and a displaceable valve disc having a plurality of spacer legs floatably disposed in said vaporization well intermediate the bottom of said electrodes and the orifice disposed in the base of said well, whereby medicated liquid disposed in said container is continuously heated by said plug which in turn is heated by the steam confined in said dome and the flow of electrolyte solution into said vaporization well is continuous for continuous formation of steam without effecting a back pressure upon the surface of the electrolyte located in the vaporization well.

*4. A thermally controlled electrically heated vaporizer for dispersing medicated vapors of the type having an upright vessel for holding a liquid, a vaporization well having an open end communicating with a jet orifice for the discharge of steam therefrom and an end disposed in the liquid in said vessel, the end of the vaporization well disposed in the liquid including a base containing an orifice for passage of the liquid from the vessel into and out of the well, and electrical heating means extending into said vaporization well with the bottom of said heating means being spaced from the base of the well, which is characterized by a disc disposed in said vaporization well intermediate the bottom of said heating means and the base of the well, said disc being of smaller area than the cross-sectional area of the interior of the vaporization well, and means for preventing the disc from closing the orifice in the base of the well.*

*5. In a thermally controlled electrically heated vaporizer for dispersing medicated vapors of the type having an upright vessel for holding an aqueous electrolyte, a vaporization well having an open end communicating with a jet orifice for the discharge of steam therefrom and an end disposed in the electrolyte in said vessel, the end of the vaporization well disposed in the electrolyte including a base containing an orifice for passage of the electrolyte from the vessel into and out of the well, and a pair of spaced-apart parallel electrodes extending into said vaporization well with the bottoms of said electrodes being spaced from the base of the well, the improvement which comprises a displaceable disc disposed in the vaporization well intermediate the bottoms of said electrodes and the base of the well, and means for preventing the displaceable disc from closing the orifice in the base of the well.*

*6. In a thermally controlled electrically heated vaporizer of the type employing a vaporization well containing a pair of spaced-apart parallel electrodes for converting water into steam, said vaporization well having a base disposed in an aqueous electrolyte, said base having an orifice therein for the passage of the electrolyte into and out of said well, said electrodes having bottoms spaced from the base of the well, the improvement which comprises a displaceable disc disposed intermediate the base of the well and the bottoms of the electrodes, said disc being of smaller area than the cross-sectional area of the vaporization well and spacing means interposed between the displaceable disc and the base of the well whereby closure of the orifice in the base of the well by said displaceable disc is prevented.*

*7. In a thermally controlled vaporizer for dispensing medicated vapors of the type employing a vaporization well disposed in an aqueous electrolyte and containing a pair of spaced-apart parallel electrodes for converting water into steam, said well communicating with a jet orifice for the discharge of steam therefrom and including a base immersed in the aqueous electrolyte, said base having an orifice therein permitting flow of the electrolyte into and out of the well, said electrodes having bottoms spaced from the base of the well, the improvement which comprises a displaceable disc disposed in said vaporization well intermediate the bottoms of said electrodes and the base of the well and a plurality of spacing legs positioned between the disc and the base of the well, said legs preventing the displaceable disc from closing the orifice in the base of the well.*

References Cited in the file of this patent or the original patent

UNITED STATES PATENTS

| | | |
|---|---|---|
| 2,140,516 | Cowan | Dec. 20, 1938 |
| 2,519,515 | Turner | Aug. 22, 1950 |
| 2,577,958 | Fisher | Dec. 11, 1951 |